US010898459B2

(12) United States Patent
Chan et al.

(10) Patent No.: US 10,898,459 B2
(45) Date of Patent: Jan. 26, 2021

(54) METHOD OF TREATING CHRONIC KIDNEY DISEASE

(71) Applicant: Panion & BF Biotech Inc., Taipei (TW)

(72) Inventors: Keith Chan, Rockville, MD (US); Winston Town, Hong Kong (CN)

(73) Assignee: Panion & BF Biotech Inc., Taipei (TW)

( * ) Notice: Subject to any disclaimer, the term of this patent is extended or adjusted under 35 U.S.C. 154(b) by 0 days.

(21) Appl. No.: 15/814,767

(22) Filed: Nov. 16, 2017

(65) Prior Publication Data
US 2018/0133191 A1 May 17, 2018

Related U.S. Application Data

(63) Continuation of application No. 12/162,543, filed as application No. PCT/US2007/002151 on Jan. 26, 2007.

(60) Provisional application No. 60/763,253, filed on Jan. 30, 2006.

(30) Foreign Application Priority Data

Aug. 18, 2006 (WO) ................ PCT/US2006/032385

(51) Int. Cl.
A61K 31/295 (2006.01)
A61K 9/14 (2006.01)
A61K 31/555 (2006.01)
A61K 33/26 (2006.01)

(52) U.S. Cl.
CPC ............ *A61K 31/295* (2013.01); *A61K 9/143* (2013.01); *A61K 31/555* (2013.01); *A61K 33/26* (2013.01)

(58) Field of Classification Search
CPC .... A61K 31/295; A61K 9/143; A61K 31/555; A61K 33/26
See application file for complete search history.

(56) References Cited

U.S. PATENT DOCUMENTS

| 2,081,547 A | 5/1937 | Mattheus |
| 3,549,614 A | 12/1970 | Zbigniew |
| 4,851,221 A | 7/1989 | Pak |
| 5,087,442 A | 2/1992 | Takaichi |
| 5,089,644 A | 2/1992 | Quay |

FOREIGN PATENT DOCUMENTS

PL 69800 A1 6/1974

OTHER PUBLICATIONS

Snively, "Chronic Kidney Disease: Prevention and Treatment of Common Complications", American Family Physican, 2004, 70 (10), pp. 1921-1928.*
Belloni, 159-212, 1920, Italian [Exhibit 2].
Viegas, Measurement of Intrinsic Drug Dissolution Rates Using Two Types of Apparatus, Pharmaceutical Technology, Jun. 2001, 44-53, USA [Exhibit 3].
Levey, et al., Definition and classification of chronic kidney disease: A position statement from Kidney Disease: Improving Global Outcomes (KDIGO), Kidney International, 2005, 67: 2089-2100 [Exhibit 4].
Snyder & Pendergraph, Detection and Evaluation of Chronic Kidney Disease. American Family Physician, 2005, 72(9): 1723-1732 [Exhibit 5].
R. Edward, Hyperphosphatemia. Encyclopedia of Endocrine Diseases, vol. 2, 2004, Elsevier, Inc. [Exhibit 6].
Kidney Disease Improving Global Outcomes (KDIGO) 2012 Clinical Practice Guideline for the Evaluation and Management of Chronic Kidney Disease, vol. 3, Issue 1, Jan. 2013 [Exhibit 7].
Alston et al., Metabolic acidosis developing during cardiopulmonary bypass is related to a decrease in strong ion difference. Perfusion, 2004, 13(3): 145-152 [Exhibit 8].
R. Niecestro et al., A Phase II, Randomized, Double-Blind, Placebo-Controlled, Dose-Ranging Study of Ferric Citrate (FC) on Serum Phosphorous Levels in ESRD Patients. SA-F0029, J. Am. Soc. Nephrol. 17 (2006): a free communication presented at the 39th Annual Meeting of the American Society of Nephrology, Nov. 16-19, 2006, San Diego. [Exhibit 9].
Keryx Biopharmaceuticals, Inc., "Keryx announces positive final results from Phase 2 dose-ranging study of Zerenex TM for the treatment of hyperphosphatemia in patients with end-stage renal disease" (published Jun. 29, 2006) [Exhibit 10].
C. Foster et al., The Washington Manual of Medical Therapeutics, 33rd ed (2010)—Hyperphosphatemia—General Principles [Exhibit 11].
Edwards R., Disorders of phosphate metabolism in chronic renal disease, Curr. Opin. Pharmacol. 2002, 2, 171-176 [Exhibit 12].
http://www.current-opinion.com/journals/current-opinion-in-pharmacology [Exhibit 13].
https://www.researchgate.net/journal/0002-838X_American_family_physician [Exhibit 14].
Albaaj, Hyperphosphataemia in Renal Failure Causes, Consequences and Current Management, Drugs, 2003, vol. 63-6, 588-596, Adis Data Information, UK [Exhibit 15].
Amin, The impact of improved phosphorus control: use of sevelamer hydrochloride in patients with chronic renal failure, Neprol Dial Transplant, 2002, 340-345, 17, European Renal Association-European Dialysis and Transplant Association, USA [Exhibit 16].
Berge, Pharmaceutical Salts, J. Pharm. Sci, Jan. 1977, vol. 66-1, 1-19, American Pharmaceutical Association, USA [Exhibit 17].
Bindroo, Renal Failure, StatPearls, Sep. 25, 2018, 1-8, StatePearls Publishing, USA [Exhibit 18].
Boclair, Layered Double Hydroxide Stability. 1. Relative Stabilities of Layered Double Hydroxides and Their Simple Counterparts, Chem. Mater., 1999, vol. 11, 298-302, American Chemical Society, USA [Exhibit 19].

(Continued)

*Primary Examiner* — Sahar Javanmard
(74) *Attorney, Agent, or Firm* — Proskauer Rose LLP; Fangli Chen

(57) ABSTRACT

The present invention discloses pharmaceutical-grade ferric organic compounds having enhanced dissolution rate. These ferric organic compounds, including but are not limited to ferric citrate, are useful for treating chronic kidney disease.

14 Claims, 6 Drawing Sheets

(56) References Cited

OTHER PUBLICATIONS

Figure 1:
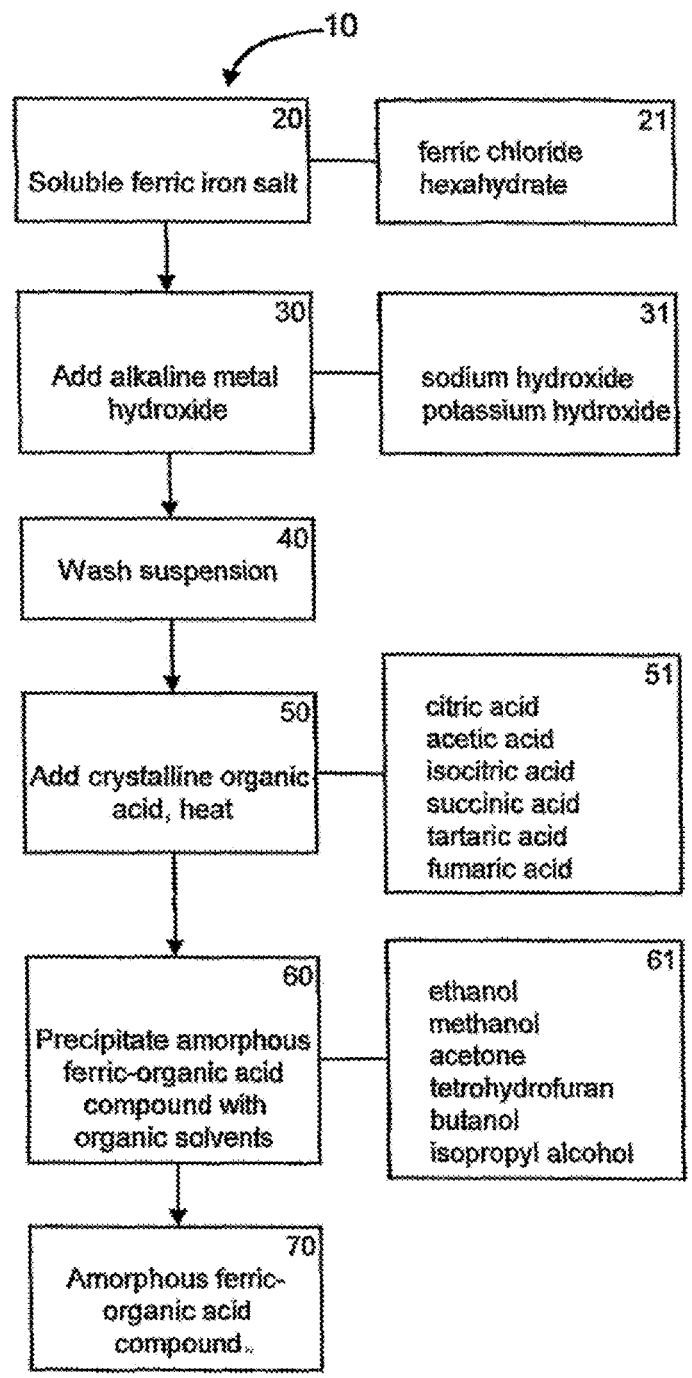

Field, Composition and Stability of Iron and Copper Citrate Complexes in Aqueous Solution, Can. J. Chem., 1974, vol. 52, 3119-3124, Canada [Exhibit 20].

Furugouri, Effect of Elevated Dietary Levels of Iron on Iron Store in Liver, Some Blood Constituents and Phosphorus Deficiency in Young Swine, J. Animal Sci., 1972, vol. 34-4, 573-577, American Society of Animal Science, USA [Exhibit 21].

Ganesh, Association of Elevated Serum PO4, Ca X PO4 Product, and Parathyroid Hormone with Cardiac Mortality Risk in Chronic Hemodialysis Patients, J Am Soc Nephrol, 2001, vol. 12, 2131-2138, American Society of Nephrology, USA [Exhibit 22].

Hegsted, The Influence of Diet on Iron Absorption II. The Interrelation of Iron and Phosphorus, 1949, 147-156, USA [Exhibit 23].

King, Pharmaceutical Sciences Chapter 90 Oral Solid Dosage Forms, 1985, Remington's, 17th edition, 1603-1632, Mack Publishing Company, USA [Exhibit 24].

Oren, Calcium oxalate kidney stones in patients on continuous ambulatory peritoneal dialysis, Kidney International, 1984, vol. 25, 534-538, International Society of Nephrology, Canada [Exhibit 25].

Ritz, Compounds in development to combat hyperphosphataemia, Expert Opin, Investig. Drugs, 2001, vol. 10-12, 2185-2190, Ashley Publication Ltd [Exhibit 26].

Timberlake, Iron-Malate and Iron-Citrate Complexes, Department of Agriculture and Horticulture, University of Bristol, 1964, 5078-5085, UK [Exhibit 27].

Warner, The Cupric and Ferric Citrate Complexes, Department of Chemistry, New York University College of Medicine, vol. 75, 1953, 5086-5094, USA [Exhibit 28].

Block, Association of Serum Phosphorus and Calcium X Phosphate Product With Mortality Risk in Chronic Hemodialysis Patients: A National Study, Am. J. Kidney Dis, 1998, vol. 31(4), 607-617, USA [Exhibit 29].

Chaumeil, Micronization: A Method of Improving the Bioavailability of Poorly Soluble Drugs, Meth Find Exp Clin Pharmacol, 1998, vol. 20(3), 211-215, Prous Science, Spain [Exhibit 30].

Stecher, The Merck Index, 1968, 8th ed., 452, Merck & Co., Inc., USA [Exhibit 31].

Lieberman, Preformulation Testing, Pharmaceutical Dosage Forms: Tablets, 1989, 2nd ed., vol. 1, 1-73, Marcel Dekker, Inc., USA [Exhibit 32].

Sheikh, Reduction of Dietary Phosphorus Absorption by Phosphorus Binders, J. Clin. Invest., 1989, vol. 83, 66-73, The American Society for Clinical Investigation, Inc., USA [Exhibit 33].

United States Pharmacopeial Convention, Intrinsic Dissolution, The United States Pharmacopeia, 2002, 25th revision, 2159-2160, United States Pharmacopeial Convention, USA [Exhibit 34].

Visek, Some Aspects of Ammonia Toxicity in Animal Cells, J. Dairy Science, 1968, vol. 51(2), 286-295, USA [Exhibit 35].

* cited by examiner

Figure 2

|  | Placebo (N=16) | | Pharmaceutical grade Ferric Citrate Phase II Clinical Study 2005 | | | | | | Chemical grade Ferric Citrate Clinical Study in Taiwan 1998 | | Chemical grade Ferric Citrate Clinical Study in U.S 1998 | |
|---|---|---|---|---|---|---|---|---|---|---|---|---|
|  |  |  | Ferric Citrate 2g/day (N=33) | | Ferric Citrate 4g/day (N=34) | | Ferric Citrate 6g/day (N=33) | | Ferric Citrate 3g/day (N=45) | | Ferric Citrate 4.5g/day (N=14) | |
|  | # Event | % | # Event | % | # Event | % | # Event | % | # Event | % | # Event | % |
| Diarrhea | 2 | 12.5% | 3 | 9.1% | 1 | 2.9% | 1 | 3.0% | 9 | 20.0% | 3 | 21.4% |
| Loose stool | 1 | 6.3% | 0 | 0.0% | 1 | 2.9% | 1 | 3.0% | 3 | 6.7% | 5 | 35.7% |
| Constipation | 0 | 0.0% | 0 | 0.0% | 2 | 5.9% | 1 | 3.0% | 4 | 8.9% | 1 | 7.1% |
| Bloating | 1 | 6.3% | 0 | 0.0% | 0 | 0.0% | 1 | 3.0% | 5 | 11.1% | 3 | 21.4% |
| Nausea | 0 | 0.0% | 2 | 6.1% | 0 | 0.0% | 1 | 3.0% | 0 | 0.0% | 0 | 0.0% |

Figure 3

Serum phosphorus (mg/dl)

| | Pharmaceutical grade Ferric Citrate Clinical Study 2005 | | | | Chemical grade Ferric Citrate Clinical Study in Taiwan 1998 | Chemical grade Ferric Citrate Clinical Study in U.S 1998 |
|---|---|---|---|---|---|---|
| | Placebo | Ferric Citrate 2g/day (N=33) | Ferric Citrate 4g/day (N=34) | Ferric Citrate 6g/day (N=33) | Ferric Citrate 3g/day (N=45) | Ferric Citrate 4.5g/day (N=14) |
| Day 0 (Baseline) | 7.2±1.4 | 7.2±1.2 | 7.1±1.3 | 7.3±1.3 | 6.7±1.9 | 7.2±2.5 |
| Day 28 (End of treatment) | 7.2±1.2 | 6.9±2.2 | 6.0±1.3 | 5.8±1.8 | 5.7±1.6 | 5.9±2.0 |
| Difference from baseline | -0.1±2.0 | -0.3±2.1 | -1.1±1.6 | -1.5±1.6 | -1.0±2.5 | -1.3±3.2 |

[Ca]x[P] (mg/dl)$^2$

| | Pharmaceutical grade Ferric Citrate Clinical Study 2005 | | | | Chemical grade Ferric Citrate Clinical Study in Taiwan 1998 | Chemical grade Ferric Citrate Clinical Study in U.S 1998 |
|---|---|---|---|---|---|---|
| | Placebo | Ferric Citrate 2g/day (N=33) | Ferric Citrate 4g/day (N=34) | Ferric Citrate 6g/day (N=33) | Ferric Citrate 3g/day (N=45) | Ferric Citrate 4.5g/day (N=14) |
| Day 0 (Baseline) | 62.8±14.0 | 62.9±13.3 | 63.5±10.7 | 65.8±12.2 | 60.8±17.1 | 60.3±15.5 |
| Day 28 (End of treatment) | 63.2±12.6 | 61.7±21.3 | 55.4±13.4 | 54.1±17.7 | 51.8±15.2 | 51.8±17.7 |
| Difference from baseline | -0.3±19.3 | -1.1±20.7 | -8.1±14.7 | -11.7±15.4 | -9.0±22.9 | -8.5±23.5 |

Mortality Rate Among Dialysis Patients With Hyperphosphatemia

METHOD OF TREATING CHRONIC KIDNEY DISEASE

This application is a Continuation of U.S. Ser. No. 14/162,543, Filed Jul. 29, 2008, which is the National Stage of International Application No. PCT/US2007/002151, Filed Jan. 26, 2007, which claims priority of International Application No. PCT/US2006/032385, Filed Aug. 18, 2006, and U.S. Ser. No. 60/763,253, Filed Jan. 30, 2006. The entire disclosures of the preceding applications are hereby incorporated by reference into this application.

Throughout this application, various publications are referenced. Disclosures of these publications in their entireties are hereby incorporated by reference into this application to more fully describe the state of the art to which this invention pertains.

FIELD OF THE INVENTION

This invention relates to the uses of pharmaceutical-grade ferric organic compounds to treat chronic kidney disease.

BACKGROUND OF THE INVENTION

Chronic kidney disease is a gradual and progressive loss of the ability of the kidneys to excrete wastes, concentrate urine, and conserve electrolytes. Unlike acute kidney failure with its abrupt but reversible of kidney function, the kidney functions in chronic kidney disease progress and deteriorate irreversibly towards end stage renal disease (ESRD). Patients suffering from ESRD cannot survive without dialysis or kidney transplantation.

The U.S. National Kidney Foundation defines chronic kidney disease according to the presence or absence of kidney damage and the level of kidney function, regardless of the type (clinical diagnosis) of kidney disease. The primary measure of kidney function is glomerular filtration rate (GFR), which is often estimated as creatinine clearance from serum and urine creatinine concentrations. Chronic kidney disease or failure is defined as having glomerular filtration rate less than 60 ml/min for three months or more. The U.S. National Kidney Foundation has suggested a five-stage classification of renal dysfunction based on glomerular filtration rate:

According to the U.S. National Kidney Foundation, there are in excess of 20 million U.S. citizens, representing approximately 11 percent of the population, suffering from chronic kidney disease, with a further 20 million at increased risk. The high prevalence rate of chronic kidney disease poses a significant burden on the healthcare system. One of the most apparent economic costs associated with chronic kidney disease is the development of end stage renal disease which, in the U.S. alone, costs approximately U.S. $23 billion in 2001 and is estimated to increase to U.S. $35 billion a year in 2010. For patients in earlier stage of chronic kidney disease, a review article has reported overall increased costs of U.S. $14,000 to U.S. $22,000 per patient per year compared to age-matched general population.

Pathogenesis of progressive renal injury is complex and multi-factorial, and the current understanding is mainly based on experimental animal models. Chronic kidney disease often progresses by "common pathway" mechanisms, irrespective of the initiating insult. Early studies of renal dysfunction focused on functional and structural glomerular changes. Recently, there has been increased interest in tubulointerstitial changes as a major determinant of progressive renal injury, and one of the key factors is the generation of calcium phosphate precipitation in urinary space and interstitum. Progression of chronic kidney disease occurs from chronic tubulointerstitial inflammation caused by increases in single nephron filtered load of phosphate, absolute tubular re-absorption of phosphate, calcium phosphate product in the tubular lumen and by precipitation of calcium phosphate in the tubules and interstitium, which is facilitated by reduced concentration of citrate in the tubular fluid (precipitation-calcification hypothesis).

The precipitation-calcification hypothesis is supported in experimental animals showing that a high phosphate diet aggravates chronic kidney disease, whereas a low-phosphate diet, administration of phosphate binders, and 3-phosphocitrate (an inhibitor of calcium phosphate precipitation) slows progression of chronic kidney disease. Based on these results, lowering serum phosphate and calcium phosphate product levels as well as increasing serum citrate and 3-phosphocitrate levels may decrease the damage of the nephron and subsequently delay the progress of chronic kidney disease. It has been reported that by slowing down Stages of renal dysfunction (adapted from National Kidney Foundation-K/DOQI)

| Stage | Description | Creatinine Clearance (~GFR: ml/min/1.73 m$^2$) | Metabolic consequences |
|---|---|---|---|
| 1 | Normal or increased GFR- People at increased risk or with early renal damage | >90 | — |
| 2 | Early renal insufficiency | 60-89 | Concentration of parathyroid hormone starts to rise (GFR~60-80) |
| 3 | Moderate renal failure (chronic renal failure) | 30-59 | Decrease in calcium absorption (GFR < 50) Lipoprotein activity falls Malnutrition Onset of left ventricular hypertrophy Onset of anaemia |
| 4 | Severe renal failure | 15-29 | Triglyceride concentrations start to rise Hyperphosphatemia Metabolic acidosis Tendency to hyperkalemia |
| 5 | End stage renal disease (Uremia) | <15 | Azotaemia develops | the progression rate of chronic kidney disease by 30% (as defined as decreasing the rate of decline in glomerular filtration rate by 30%) between 2000 and 2010, the estimated potential cumulative direct healthcare savings would be US $60.61 billion.

Hyperparathyroidism is one of the earliest manifestations of impaired renal function, and minor changes in bone have been found in patients with a glomerular filtration rate of 60 ml/min (chronic kidney disease stage 2 to 3). With the worsening of kidney condition and phosphorus accumulation, parathyroid will continuously increase the release of parathyroid hormone (PTH) and lead to the development of hyperparathyroidism. High PTH will increase calcium release from bone to serum. The result is abnormal serum concentrations of calcium and phosphorus and lead to bone disease and extraskeletal calcification. Precipitation of calcium phosphate in renal tissue begins early. This may influence the rate of progression of renal disease, and is closely related to hyperphosphatemia and calcium phosphate (Ca×P) product.

Acid-base balance is normally maintained by renal excretion of the daily acid load. As renal function declines, the acid-base balance is maintained by various compensatory mechanisms, of which an increase in the synthesis of ammonia by proximal tubule is the most important. A defective trapping of ammonia in the medulla poses further demands on proximal tubules to increase synthesis of ammonia and results in an enhanced concentration of ammonia in renal cortex. High concentration of free-base ammonia in renal cortex can result in complement activation and interstitial inflammation which has been reported to be one of the major determinant of progressive renal injury. Renal acidosis result in bone demineralization, hyperparathyroidism, increase protein catabolism, insulin resistance and stunted growth. Recent observations suggest that acidosis triggers inflammation and accelerates progression of chronic kidney disease.

Chronic metabolic acidosis can result in protein metabolism and thus increased excretion of urate and formation of kidney stones. If not treated, kidney stone could cause urine obstruction, urinary tract infection and may result in development of chronic kidney disease.

Once the degeneration process of kidney begins, there is no cure for chronic renal failure to date. As a preventive measure at the early stage, it has been suggested to identify and treat the underlying condition as urinary track infection, obstruction, kidney stone or stop taking drugs with nephrotoxic effects (i.e., NSAIDs) before chronic kidney disease can be developed. It is also suggested to change diet plans (i.e., low protein diet) in the early stage. In addition, hypertension and diabetes have been identified as the most common risk factors of the disease. The benefits of using antihypertensive therapy on the progression of chronic kidney disease have been extensively examined. Uses of angiotension converting enzyme inhibitors (ACEIs) and angiotension receptor blockers (ARBs) have shown to be beneficial among patients with or without diabetes as well as those with or without proteinuria.

However, in reality many physicians fail to use these drug classes in patients with renal insufficiency because these two classes of drug may potentially increase the level of either serum creatinine (an indication of renal deterioration) or potassium (most common life-threatening emergency in patient with end stage renal disease). It has been suggested that these drugs not to be used in patients with advanced renal failure, bilateral renal artery stenosis, and renal artery stenosis in a solitary kidney. Therefore, these drugs appear not to be commonly used on patients who already developed renal disease, and these drugs are not expected to delay the progression of chronic kidney disease.

In additional to treating or preventing progression of chronic kidney disease, other medications such as iron and erythropoietin supplements are needed to control anemia in chronic kidney disease patients. $NaHCO_3$ is used to ameliorate one of the uremic syndromes such as metabolic acidosis which leads to osteopenia and urinary calcium excretion.

Ferric iron containing compounds are useful in the treatment of a number of disorders, including, but not limited to, hyperphosphatemia and metabolic acidosis. See Hsu et al., New Phosphate Binding Agents: Ferric Compounds, J Am Soc Nephrol. 10:1274-1280 (1999). Previous studies and inventions have reported the use of ferric compounds in binding dietary phosphates, and such ferric compounds are potentially useful for the treatment of hyperphosphatemia in renal failure patients (U.S. Pat. Nos. 5,753,706; 6,903,235; CN 1315174; Yang et al., Nephrol. Dial. Transplant 17:265-270 (2002)). Elevated amounts of phosphate in the blood can be removed by administering compounds such as ferric citrate. Once in solution, the ferric iron binds phosphate, and the ferric phosphate compounds precipitate in the gastrointestinal tract, resulting in effective removal of dietary phosphate from the body. It is also believed that the absorbed citrate from ferric citrate is converted to bicarbonate which corrects metabolic acidosis, a condition common in renal failure patients.

U.S. Pat. No. 5,753,706 discloses the use of ferric containing compounds, including ferric citrate and ferric acetate in the crystalline form, in an orally effective 1 gram dosage form to bind to soluble dietary phosphate, thus causing precipitation of phosphate as ferric or ferrous phosphates in the gastrointestinal tract and preventing oral absorption of soluble phosphates from dietary sources. Since binding of ferric ions to soluble phosphate in the gastrointestinal tract would require dissolution of the orally administered ferric citrate, and since the rate of dissolution of crystalline ferric citrate is slow (over 10-12 hours at 37° C.), oral administration of a substantially large dose of 1 g of ferric citrate is required. A related Chinese patent application (CN 1315174) also discloses a similar use of ferric citrate and related compounds in an oral solution dosage form for the treatment of hyperphosphatemia in renal failure patients.

Fe (III) is a Lewis acid and is chemically less soluble in the stomach at pH below 5 than at intestinal pH normally above 7. The stomach is, however, believed to be an important site of action for the dissolution of Fe (III) compounds. It is believed that the stomach is an important site of action for Fe (III) to mediate its action in binding to dietary phosphates, preventing phosphate from reaching the intestine and thus reducing absorption of phosphates from the intestine.

Int'l App. No. PCT/US2004/004646, filed Feb. 18, 2004, published under Int'l Publication No. WO2004/074444 on Sep. 2, 2004, discloses a method of preparing novel ferric organic compounds, including ferric citrate that has a large active surface area, and remains soluble over a wider range of pH than previously described preparations. This publication also teaches using these novel ferric organic compounds in the treatment of various disorders such as hyperphosphatemia and metabolic acidosis. Because they are more soluble, these novel forms of ferric organic compounds can be used to more effectively deliver ferric organic compounds by the route of oral administration to patients. However, this publication did not provide any data to show whether these novel forms of ferric organic compounds would be useful in providing treatment for patients with chronic kidney disease.

The present invention discloses these novel forms of ferric organic compounds possess several characteristics beneficial for the treatment or modification of chronic kidney disease.

SUMMARY OF THE INVENTION

In accordance with these and other objects of the invention, a brief summary of the present invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

The present invention provides a method of treating a subject having chronic kidney disease, comprising administering to said subject an effective amount of a ferric organic compound that has a dissolution rate of at least approximately 2 $mg/cm^2/min$. An example of ferric organic compound is ferric citrate. Representative ranges of the dissolution rate include, but are not limited to, from about 2.5 $mg/cm^2/min$ to about 3.0 $mg/cm^2/min.$, or from about 3.0 $mg/cm^2/min$ to about 3.5 $mg/cm^2/min.$, or from about 3.5 $mg/cm^2/min$ to about 4.0 $mg/cm^2/min$.

In one embodiment, the ferric organic compound is prepared according a method comprising the steps of: (a) obtaining a ferric iron salt; (b) adding an alkaline metal hydroxide to the ferric iron salt under conditions effective to produce a mixture comprising polyiron oxide; (c) isolating a precipitate from the mixture; (d) adding an organic acid to the precipitate; (e) forming a ferric organic acid solution by heating the organic acid and the precipitate; and (f) precipitating the ferric organic compound from the ferric organic acid solution by adding an organic solvent to the solution.

In general, a subject is a human or an animal. The subject may have any stage of chronic kidney disease (e.g. end stage renal disease), or is undergoing renal dialysis. The ferric organic compound may be administered orally or any other appropriate route generally known in the art and the ferric organic compound can be formulated into a number of formats generally known in the art. Representative formats include, but are not limited to, a tablet, a powder, a suspension, an emulsion, a capsule, a lozenge, a granule, a troche, a pill, a liquid, a spirit, or a syrup.

In one embodiment, treatment with the ferric organic compound results in decreased serum creatinine and BUN level in the subject. In another embodiment, treatment with the ferric organic compound results in decreased phosphorus and calcium and phosphorus product (Ca×P) levels in serum.

In one embodiment, treatment with the ferric organic compound would prevent, reverse, maintain, or delay progression of chronic kidney disease. In another embodiment, development of hyperparathyroidism, bone disorder, or cardiovascular disease in the subject is prevented, reversed, maintained or delayed. In yet another embodiment, calcium phosphate precipitation in the subject's renal tissue is prevented, reversed, maintained or delayed. In yet another embodiment, kidney stone formation is prevented, reversed, maintained or delayed. In still yet another embodiment, development of metabolic acidosis in the subject is prevented, reversed, maintained or delayed.

The present invention also provides uses of a ferric organic compound described herein for preparation of a medicament for treating a subject having chronic kidney disease.

The present invention also provides a method of treating a subject having chronic kidney disease, comprising administering to said subject an effective amount of a ferric organic compound. An example of the ferric organic compound is ferric citrate. In one embodiment, the ferric organic compound has a dissolution rate of at least approximately 2 $mg/cm^2/min$.

The present invention also provides a therapeutic regimen for treating a subject having chronic kidney disease; the regiment comprises a pharmaceutical composition comprising an acceptable carrier and an effective amount of ferric organic compound having a dissolution rate of at least 2 $mg/cm^2/min.$, wherein the pharmaceutical composition is administered in single or multiple doses regimens.

The present invention also provides a pharmaceutical composition for treating a subject having chronic kidney disease, the composition comprising an effective amount of a ferric organic compound having a dissolution rate of at least approximately 2 $mg/cm^2/min$.

The present invention also provides a use of the above pharmaceutical composition in preparation of a medicament for treating a subject having chronic kidney disease.

DETAILED DESCRIPTION OF THE FIGURES

In drawings which illustrate specific embodiments of the invention, but which should not be construed as restricting the spirit or scope of the invention in any way:

FIG. 1 is a schematic diagram outlining the method of making novel forms of ferric organic compounds according to the present invention.

Figure 4:
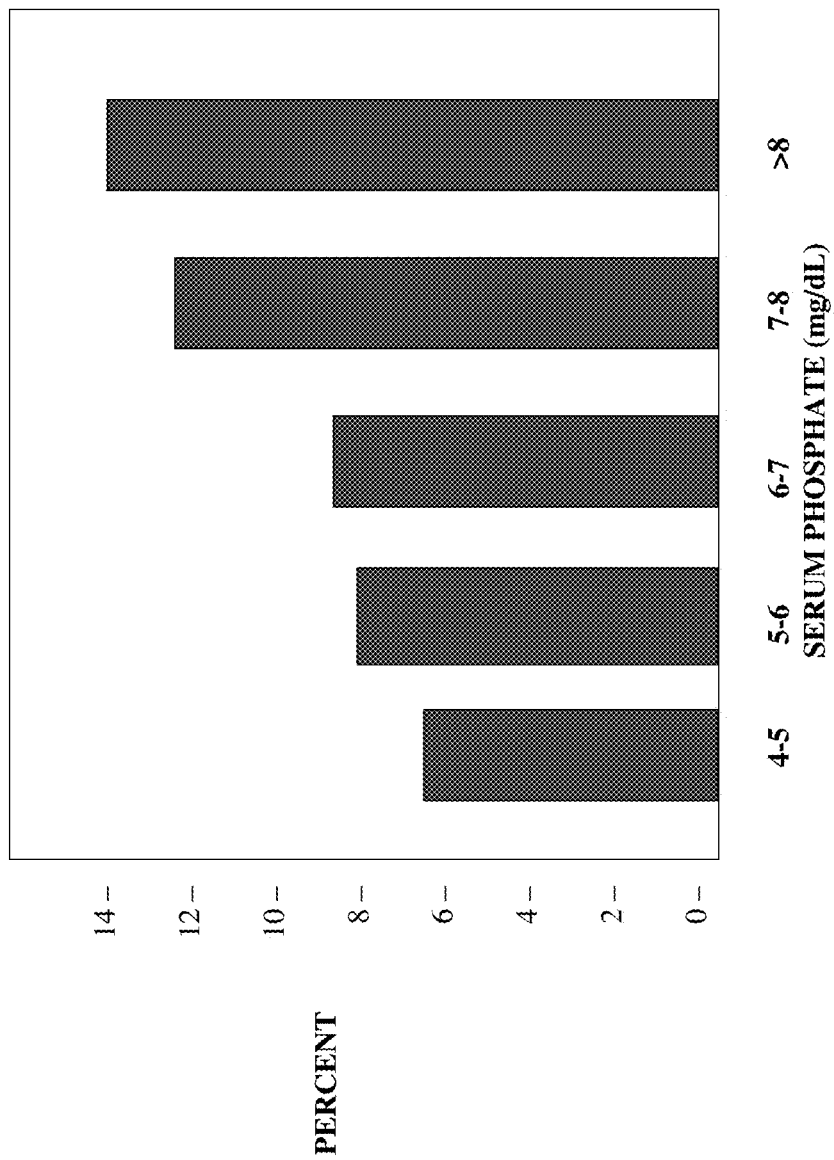
Figure 5:
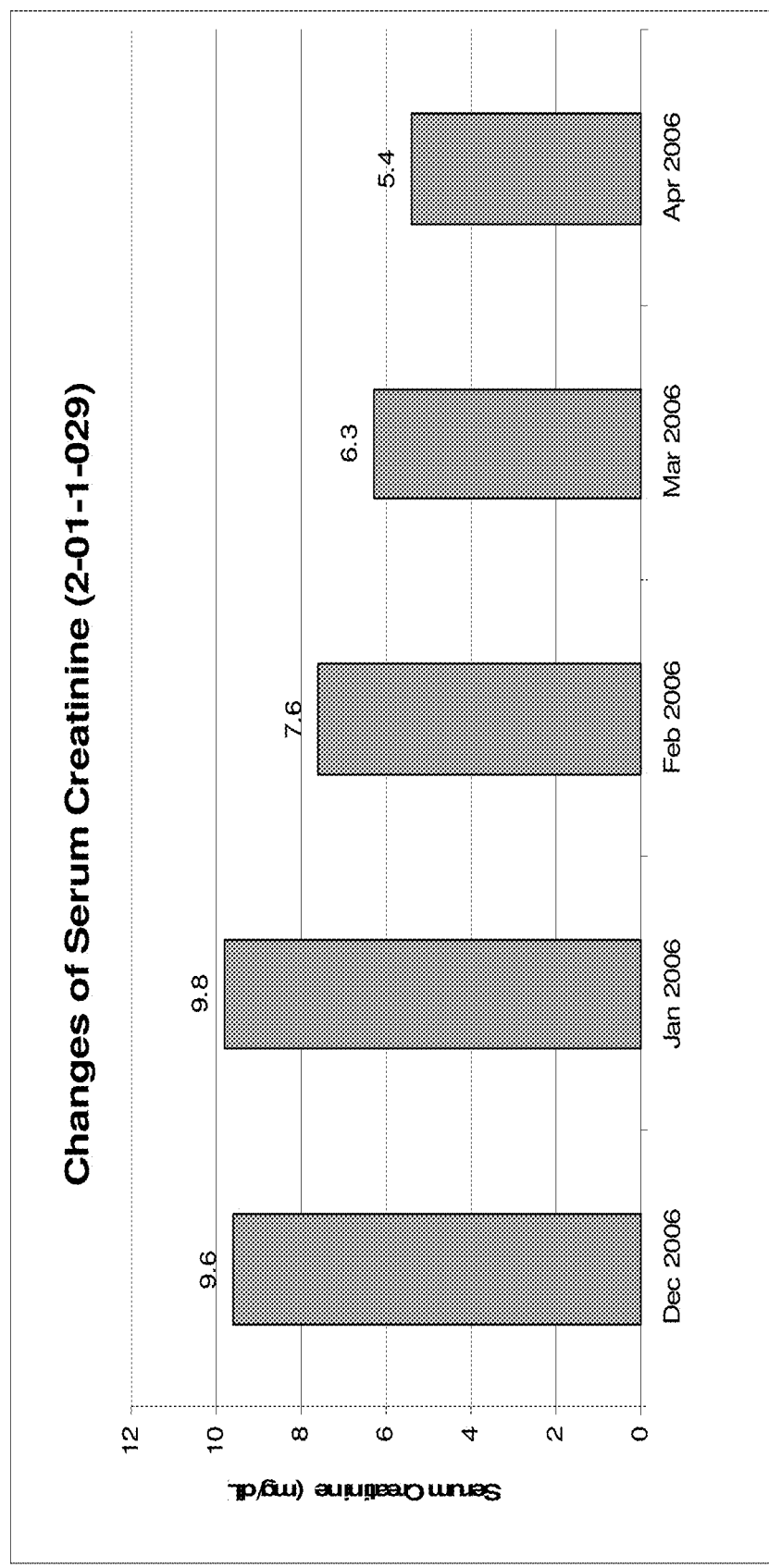

FIG. 2 is a comparison of the safety profiles of chemical grade and pharmaceutical grade ferric citrates FIG. 3 is a comparison of the efficacy profiles of chemical grade and pharmaceutical grade ferric citrates FIG. 4 shows a bar graph of the relationship between the rate of dialysis patient mortality and hyperphosphatemia FIG. 5 shows the serum creatinine levels of a patient (patient code: 2-01-1-029) treated with 6 g/day of ferric citrate.

Figure 6:
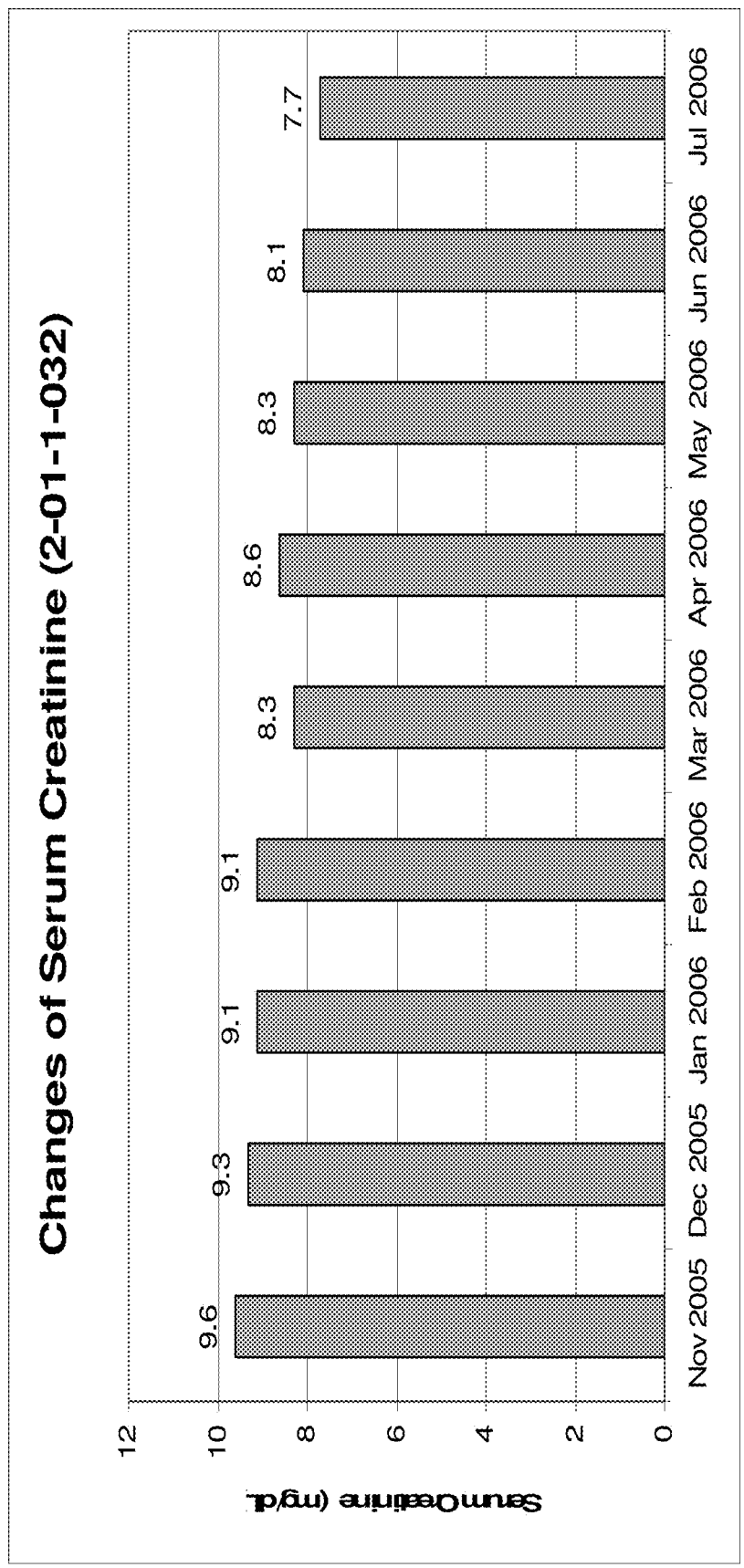

FIG. 6 shows the serum creatinine levels of a patient (patient code: 2-01-1-032) treated with 6 g/day of ferric citrate.

DETAILED DESCRIPTION OF THE INVENTION

In drawings which illustrate specific embodiments of the invention, but which should not be construed as restricting the spirit or described in detail to avoid unnecessarily obscuring the invention. Accordingly, the specification and drawings are to be regarded in an illustrative, rather than a restrictive, sense.

Results presented below indicate that treatment with ferric citrate, an example of ferric organic compounds produced according to the methods described herein, would reduce serum concentrations of creatinine, phosphorus, calcium, and phosphorus product (Ca×P) in patients with chronic kidney disease. Hence, ferric organic compounds of the present invention, including but not limited to ferric citrate, can be used to modify the progression of chronic kidney disease (CKD) in a subject; for example, the progression of CKD can be prevented, reversed, maintained, or delayed.

The present invention is not limited to using the ferric citrate disclosed herein. Other ferric citrate compounds, or their salts, derivatives, analogs, metabolites, or preparations that are suitable for use in the methods of the present invention will be readily apparent to a person of ordinary skill in the art by following the teaching of this application. Furthermore, methods of the present invention also encompass using other ferric organic compounds synthesized according to the methods described herein. These ferric organic compounds preferably have or include the following properties:

high affinity for binding phosphorous;
soluble over a wide range of pH;
rapid binding independent of pH;
high solubility;
low absorption throughout the entire body;
lack of toxicity;
can be administered orally; and/or
inexpensive to produce.

In view of the data presented herein, one of ordinary skill in the art would also readily realize that the present invention is not limited to using ferric organic compounds produced according to the method disclosed herein. Hence, it will be readily apparent to a person of ordinary skill in the art that the present invention encompasses methods of using ferric organic compounds to treat chronic kidney disease, wherein the ferric organic compounds possess certain characteristics as described herein.

In one embodiment, the ferric organic compounds produced according to the methods described herein are useful in the treatment of hyperphosphatemia, metabolic acidosis, and any other disorders responsive to ferric organic compound therapy. Because the ferric organic compounds of the present invention are more soluble than commercially available ferric organic compounds, smaller amounts of the ferric organic compounds of the present invention can be used to effectively treat patients suffering from such disorders.

In one embodiment of the invention, the ferric citrate of the present invention has a significantly higher rate of aqueous solubility under physiological conditions than commercially available forms of ferric citrate, and therefore the ferric citrate of the present invention is believed to provide a significant improvement in the orally effective use of ferric citrate at a reduced dosage. By reducing the orally effective dose of ferric citrate, it is believed that the ferric citrate of the present invention will provide a lower incidence of ulcerative gastrointestinal adverse effects associated with commercially available ferric citrate compounds. In addition, it is believed that the increased rate of dissolution of the ferric citrate of the present invention will provide a more rapid onset of action in binding to dietary phosphate. Furthermore, the ferric organic compounds of the present invention are more soluble over a wider pH range than commercially available ferric organic compounds; therefore, the ferric organic compounds of the present invention can be more effective by being soluble in the small intestine.

The ferric organic compounds of the present invention can be administered in a number of forms generally known in the art. Pharmaceutical compositions comprising the ferric organic compounds of the present invention include, but are not limited to solids, liquids, or semi-solid forms, such as gels, syrups, chewables or pastes. The ferric organic compounds of the present invention can be administered alone or in combination with a pharmaceutically acceptable carrier. Orally administrable forms include, but are not limited to, a tablet, a powder, a suspension, an emulsion, a capsule, a granule, a troche, a pill, a liquid, a spirit, or a syrup. The composition can be administered to human beings or other animals suffering from illnesses responsive to ferric organic compound therapy.

An effective amount of pharmaceutical-grade ferric citrate can be readily determined by one of ordinary skill in the art. For example, an effective dose may be from 2 to 100 grams per day, preferably between 2 and 60 grams per day. Alternatively, a daily effective amount may be 2, 4, 6, or 8 grams.

Compositions comprising pharmaceutical grade ferric organic compounds of the present invention, such as ferric citrate, are suitable for treating hyperphosphatemia, or other disorders characterized by high serum phosphate levels. Therefore, the invention encompasses treating subjects or patients with various renal diseases; e.g., End Stage Renal Diseases (ESRD), Chronic Kidney Disease (CKD) or other relate kidney diseases, or subjects and patients who are on dialysis but not limited to hemodialysis.

In one embodiment, compositions comprising pharmaceutical grade ferric organic compounds of the present invention, such as ferric citrate, may be used to treat subjects or patients with metabolic acidosis. Other disorders that may be ameliorated by the conversion of citrate to bicarbonate are also encompassed by the invention described.

In one embodiment, a method for using the pharmaceutical composition encompasses treating a human or non-human subject or patient with chronic kidney disease. There are generally five clinical stages of chronic kidney disease, numbered 1 to 5, wherein stage 1 is the least severe and stage 5 the most severe. In the early stages, e.g., stages 1 and 2, dialysis is not required. As chronic kidney disease progresses to stage 5, a patient may require dialysis treatment three times per week. It should be noted that elevated phosphate levels are observed at all stages of chronic kidney disease. Therefore, an embodiment of the invention is a method of treating a subject or person with early or mid-stage chronic kidney disease, with a composition comprising pharmaceutical-grade ferric citrate in order to achieve a lower serum phosphate level.

In another embodiment, there is provided a method of treating a human or non-human subject or patient with late-stage chronic kidney disease who is undergoing hemodialysis, by administering a composition comprising pharmaceutical-grade ferric citrate of the present invention. It is generally known that hemodialysis is not sufficiently effective in reducing serum phosphate level. The treatment of a subject or person with late stage kidney disease is applicable whether or not the subject or person is currently undergoing hemodialysis treatment.

An additional embodiment of the invention is a method of treating a subject or person with chronic kidney disease and undergoing peritoneal dialysis with the pharmaceutical-grade ferric citrate-containing compositions described herein. It is known that peritoneal dialysis is not sufficiently effective in reducing serum phosphate levels.

The present invention provides a method of treating a subject having chronic kidney disease. In general, the subject is a human or an animal. The subject may have end stage renal disease, or is undergoing renal dialysis. The method comprises the steps of administering to said subject an effective amount of a ferric organic compound that has a dissolution rate of at least approximately 2 mg/cm$^2$/min. Representative ranges of the dissolution rate include, but are not limited to, from about 2.5 mg/cm$^2$/min to about 3.0 mg/cm$^2$/min., or from about 3.0 mg/cm$^2$/min to about 3.5 mg/cm$^2$/min., or from about 3.5 mg/cm$^2$/min to about 4.0 mg/cm$^2$/min.

In one embodiment, the ferric organic compound is prepared according a method comprising the steps of: (a) obtaining a ferric iron salt; (b) adding an alkaline metal hydroxide to the ferric iron salt under conditions effective to produce a mixture comprising polyiron oxide; (c) isolating a precipitate from the mixture; (d) adding an organic acid to the precipitate; (e) forming a ferric organic acid solution by heating the organic acid and the precipitate; and (f) precipitating the ferric organic compound from the ferric organic acid solution by adding an organic solvent to the solution.

In one embodiment, the alkaline metal hydroxide is sodium hydroxide, the ferric iron salt is ferric chloride hexahydrate, and the organic acid is crystalline citric acid.

In general, the alkaline metal hydroxide (e.g. sodium hydroxide or potassium hydroxide) is added at a rate of less than 20 ml/min, preferably between about 10 ml/min to about 20 ml/min., and the alkaline metal hydroxide is added to the ferric iron salt at a temperature of less than 40° C., preferably between about 10° C. to about 40° C. The organic acid and the precipitate are heated to a temperature of between about 80° C. to about 90° C. Precipitating the ferric organic compound from the ferric organic acid solution by an organic solvent comprises cooling the ferric organic acid solution to less than 30° C. before adding the organic solvent, preferably the ferric organic acid solution is cooled to a temperature between about 10° C. to about 30° C.

A number of organic acids, such as citric acid, acetic acid, isocitric acid, succinic acid, fumaric acid, and tartaric acid can be used in the method of synthesizing the ferric organic compound. In one embodiment, the organic acid is in crystalline form. Moreover, a number of organic solvent, such as ethanol, methanol, butanol, isopropyl alcohol, acetone, and tetrahydrofuran can be used in synthesizing the ferric organic compound described herein.

The ferric organic compound can be administered at an effective dose determined by one of ordinary skill in the art, for example 2-20 gm/day. The ferric organic compound can be administered orally or any other appropriate route readily determined by one of ordinary skill in the art. In general, the ferric organic compound can be formulated as a tablet, a powder, a suspension, an emulsion, a capsule, a lozenge, a granule, a troche, a pill, a liquid, a spirit, or a syrup.

In one embodiment, treatment with the ferric organic compound results in decreased serum creatinine and BUN level in the subject. In another embodiment, treatment with the ferric organic compound results in decreased phosphorus, calcium, and phosphorus product (CaxP) levels in serum.

In one embodiment, treatment with the ferric organic compound would prevent, reverse, maintain, or delay progression of chronic kidney disease. In another embodiment, development of hyperparathyroidism, bone disorder, or cardiovascular disease in the subject is prevented, reversed, maintained or delayed. In yet another embodiment, calcium phosphate precipitation in the subject's renal tissue is prevented, reversed, maintained or delayed. In yet another embodiment, kidney stone formation is prevented, reversed, maintained or delayed. In still yet another embodiment, development of metabolic acidosis in the subject is prevented, reversed, maintained or delayed.

The present invention also provides a method of treating a subject having chronic kidney disease, comprising administering to said subject an effective amount of a ferric organic compound, wherein the ferric organic compound is prepared according a method comprising the steps of: (a) obtaining a ferric iron salt; (b) adding an alkaline metal hydroxide to the ferric iron salt under conditions effective to produce a mixture comprising polyiron oxide; (c) isolating a precipitate from the mixture; (d) adding an organic acid to the precipitate; (e) forming a ferric organic acid solution by heating the organic acid and the precipitate; and (f) precipitating the ferric organic compound from the ferric organic acid solution by an organic solvent. This method of synthesis has been described herein to produce ferric organic compound (e.g. ferric citrate) that has enhanced dissolution rate (e.g. a dissolution rate of at least about 2 mg/cm$^2$/min.). This method of treatment would produce therapeutic effects described above.

The present invention also provides a method of treating a subject having chronic kidney disease, comprising administering to said subject an effective amount of a ferric organic compound. Examples of ferric organic compound include, but are not limited to, ferric citrate. In general, the subject is a human or an animal. The subject may have end stage renal disease, or is undergoing renal dialysis. In one embodiment, the ferric organic compound has a dissolution rate of at least approximately 2 mg/cm$^2$/min.

The present invention also provides a therapeutic regimen for treating a subject having chronic kidney disease, the regiment comprises a pharmaceutical composition comprising an acceptable carrier and an effective amount of ferric organic compound having a dissolution rate of at least 2 mg/cm$^2$/min., wherein the pharmaceutical composition is administered in single or multiple doses regimens. An example of ferric organic compound is ferric citrate. As shown in Table 1, a ferric organic compound such as ferric citrate having a dissolution rate of at least 2 mg/cm$^2$/min. would be useful in the present method. For example, the dissolution rate of the ferric organic compound can be from approximately 2.5 mg/cm$^2$/min to approximately 3.0 mg/cm$^2$/min., or from approximately 3.0 mg/cm$^2$/min to approximately 3.5 mg/cm$^2$/min., or from approximately 3.5 mg/cm$^2$/min to approximately 4.0 mg/cm$^2$/min. In general, at least a portion of the pharmaceutical composition is administered orally. In one embodiment, the subject is having end stage renal disease, and the method may optionally comprise renal dialysis or peritoneal dialysis.

The present invention also provides a pharmaceutical composition for treating a subject having chronic kidney disease, the composition comprising an effective amount of a ferric organic compound (e.g. ferric citrate) having a dissolution rate of at least approximately 2 mg/cm$^2$/min. In one embodiment, the dissolution rate is from about 2 mg/cm$^2$/min to about 4 mg/cm$^2$/min. In general, the composition is in a form suitable for oral administration, e.g. as a tablet, a powder, a suspension, an emulsion, a capsule, a lozenge, a granule, a troche, a pill, a liquid, a spirit, or a syrup.

The present invention also provides a use of the above pharmaceutical composition in preparation of a medicament for treating a subject having chronic kidney disease. In one embodiment, the subject is having end stage renal disease or undergoing renal dialysis.

The following examples are intended to illustrate embodiments of the invention but which are not intended to limit the scope of the invention.

Example 1

General Method for Synthesis of a Pharmaceutical-Grade Ferric Organic Compound

General methods for the synthesis of ferric organic compounds have been disclosed in PCT/US2006/032585, and U.S. provisional application No. 60/763,253, which are incorporated by reference into this application. Representative ferric organic compounds include, but are not limited to, ferric citrate.

Referring to FIG. 1, the flowchart 10 is a general process for synthesizing a form of ferric organic compound or ferric citrate compound which can be used in the present invention. The starting materials, as indicated in box 20, comprise soluble ferric iron salts. The soluble ferric iron salts can comprise ferric chloride hexahydrate ($FeCl_3 6H_2O$), as indicated in box 21, or any other suitable soluble ferric iron salt. Next, an alkaline metal hydroxide (box 30) is added at a specific rate and temperature to the soluble ferric iron salt. The addition of the alkaline metal hydroxide at a specific rate, preferably between about 10 ml/min and about 20 ml/min, and temperature range, preferably below 40° C., results in the formation of a uniform polyiron oxo colloidal suspension. The alkaline metal hydroxide can comprise sodium hydroxide, potassium hydroxide, or any other suitable alkaline metal hydroxide as indicated in box 31.

The colloidal suspension precipitate is collected and rinsed (box 40) with distilled water to remove any soluble impurities. After rinsing, the precipitate is re-suspended and, as indicated in box 50, crystalline organic acid is added to the precipitate and heated to a particular temperature range, preferably between about 80° C. to about 90° C. The organic acid can comprise any suitable organic acid. Box 51 lists some of the possible organic acids which can be used, including, but not limited to, citric acid, acetic acid, isocitric acid, succinic acid, fumaric acid, and tartaric acid. The addition of the organic acid allows the acid to form complexes with the precipitate in solution. At box 60, the ferric organic compound is precipitated out of solution with an organic solvent to form a novel form of ferric organic compound (box 70). Various organic solvents can be used, including, but not limited to, the solvents described in box 61, such as ethanol, methanol, butanol, acetone, isopropyl alcohol, tetrahydrofuran, or any other suitable organic solvent.

Synthesis of Ferric Citrate

In one embodiment of the invention, the ferric organic compound is ferric citrate. The starting materials for making a ferric citrate comprise a 1.85M solution of ferric chloride hexahydrate ($FeCl_3 6H_2O$). A volume of 5M sodium hydroxide necessary to produce a 1:3 ratio of ferric iron to hydroxide ion is added to the ferric chloride hexahydrate solution at a rate of less than 20 ml per minute, preferably between about 10 ml per minute and about 20 ml per minute. The temperature of the mixture is maintained below 40° C., preferably between about 10° C. to about 40° C., while the sodium hydroxide is added to form a polyiron oxide colloidal suspension of ferric hydroxide. The pH of the suspension is measured while the sodium hydroxide is added. Once the pH is above 7.0, the suspension is cooled until it is less than 30° C., preferably between about 10° C. to about 30° C. The suspension is then filtered through a 1 mm pore filter to breakup aggregates and large particles of ferric hydroxide precipitate are then removed. The filtered ferric hydroxide suspension is then centrifuged. The supernatant is discarded, and the precipitated ferric hydroxide is centrifuged again to remove any remaining supernatant. The ferric hydroxide precipitate is then resuspended with distilled water. The centrifugation-resuspension steps are repeated two more times to wash the ferric hydroxide precipitate and remove water soluble impurities. The resulting ferric hydroxide precipitate is then homogenized.

An amount of citric acid necessary to produce a 1:1 ratio of ferric iron to citrate is added to the precipitate. The mixture is heated to between about 80° C. to about 90° C. in an oil bath until the color of the mixture changes from orange-brown to a clear black-brown, or until all of the ferric hydroxide precipitate is dissolved. The reaction is cooled until it is less than 30° C., preferably between about 10° C. to about 30° C., and the pH is measured to determine that it is within 0.8 and 1.5. The reaction is centrifuged, and the supernatant is collected. Ferric citrate is precipitated from the supernatant by adding 5 volumes of organic solvent.

Various organic solvents can be used, including ethanol, methanol, butanol, acetone, isopropyl alcohol, or tetrahydrofuran. Once the solvent is added, the mixture is stirred until a light beige precipitate forms. The suspension is centrifuged and the supernatant is discarded. The precipitate is washed and centrifuged with the solvent two more times. The precipitate is then dried in a vacuum oven for 8 to 16 hours at ambient temperature or by any other suitable industrial processes such as fluidized-bed drying. The dried precipitate is ground with a mortar and pestle and dried for another 8 to 24 hours at ambient temperature. The fine precipitate is finely ground by milling again and screened through a 45 mesh size (35 micron) sieve. The novel form of ferric citrate powder is dried in the vacuum oven again or fluidized-bed drying again and dried at ambient temperature until 1 hour of drying leads to less than 0.25% loss in weight.

Example 2

Solubility Profile of Ferric Organic Compounds According to the Invention

The ferric organic compounds produced according to the methods described above are more soluble than commercially available ferric organic compounds, over a wider range of pH levels. This increase in solubility of the ferric organic compounds of the present invention is believed to be a result of the unique significantly large active surface area of the ferric organic compounds of the present invention. For example, at pH 8.0, the intrinsic dissolution rate of ferric citrate of the present invention is 3.32 times greater than the commercially available ferric citrate. See Table 1.

The intrinsic dissolution rates of commercially available ferric citrate were compared with the ferric citrate of the present invention. The intrinsic dissolution rate is defined as the dissolution rate of pure substances under the condition of constant surface area. The dissolution rate and bioavailability of a drug substance is influence by its solid state properties: crystallinity, amorphism, polymorphism, hydration, solvation, particle size and particle surface area. The measured intrinsic dissolution rate is dependent on these solid-state properties and is typically determined by exposing a constant surface area of a material to an appropriate dissolution medium while maintaining constant temperature, stirring rate, and pH. The intrinsic dissolution rates are presented in Table 1.

TABLE 1

Intrinsic Dissolution Rates of Ferric Citrate
at 37° C. in Solutions of pH 8

| Sample | Rate of Acetone Addition (ml/min) | Intrinsic Dissolution Rates (mg/cm²/min) | Mean Intrinsic Dissolution Rates (mg/cm²/min) |
|---|---|---|---|
| RFS-12 (sigma/commercially available) | 10.0 | 0.83 | 0.83 |
| STM-134 (reference material) | 10.0 | 1.88 | 1.88 |
| PAN031203A (experimental batch 1) | 10.0 | 3.82 | 3.32 |
| PAN031203B (experimental batch 2) | 10.0 | 4.00 | |
| PAN031203C (experimental batch 3) | 9.5 | 2.68 | |
| PAN031203D (experimental batch 4) | 40 | 2.95 | |
| PAN031203E (experimental batch 5) | 4.4 | 3.13 | |

The BET active surface area of the ferric citrate of the present invention is at least 16 times larger than the commercially available ferric citrate. See Table 2.

The analysis of active surface area is based on BET theory which describes the phenomenon of mass and energy interaction and phase changes during gas adsorption onto solid surfaces and in pore spaces. In BET active surface area measurement, the volume of a monolayer of gas is determined which allows the surface area of the sample to be determined using the area occupied by a single layer of adsorbed gas molecule. Table is a comparison of the active surface area of the ferric citrate of the present invention compared to the active surface area of commercially available ferric citrate compounds.

TABLE 2

BET Active Surface Areas of Various Forms of Ferric Citrate

| Sample | Mean Dissolution Rates (mg/cm2/min) | BET Active Surface Area |
|---|---|---|
| RFS-12-1 (sigma/commercially available) | 0.76 | 0.61 |
| RFS-12-2 (sigma/commercially available) | | |
| STM-134-1 (reference material 1) | 2.47 | 16.17 |
| STM-134-2 (reference material 2) | | |
| STM-182-1 (lab-scale 500 g batch 1) | 2.61 | 19.85 |
| STM-182-2 (lab-scale 500 g batch 2) | | |

Example 3

Methods of Using and Testing the Pharmaceutical-Grade Ferric Citrate in Patients Handling and Forms of Test Compositions Ferric citrate is supplied in 500 mg capsules, whereas the placebo will be provided in identical-looking capsules (indistinguishable from those containing the active drug); the placebo capsules will contain sorbitol and colorant to match the powder color of the active capsules. The placebo capsule shells will be identical to the active capsule shells.

Storage

All study drug supplies must be stored under secure conditions and are not to be used after their expiration date, which is imprinted on the study drug container. The study drugs should be kept under controlled conditions (15 to 30° C.; 59 to 86° F.) in a tightly closed container, protected from light.

Dosage

A recent pilot study compared ferric citrate (3 g daily) to calcium carbonate (3 g daily) for reducing serum $PO_4$ in patients with End Stage Renal Disease (ESRD). This dose of ferric citrate was associated with mild, but tolerable GI symptoms.

The doses of ferric citrate chosen for study or treatment may be from 1 to 30 grams of ferric citrate per day. In part, this may depend on the nature of the formulation provided. For example, ferric citrate capsules may be administered up to a daily dose of about 15 grams/day, whereas the tablet form may be administered up to 30 grams/day. Thus, there is a very broad range of dosing regimens encompassed by the invention.

Titration of Optimal Dosage for a Subject

In the context of this invention, the term "subject" refers to either a human or non-human animal. The optimal dosage of an individual subject or groups may be determined as follows. A dose of approximately one or two grams per day is merely suggested as an illustrative starting dose. The daily dose may be increased as needed until the desired result is observed.

The intent of the invention is to not limit the dose range employed. Therefore, depending on the subject(s) the daily dose administered may approximate thirty, forty, fifty, sixty, seventy, eighty, ninety or one hundred grams per day. The safety profile of the pharmaceutical-grade ferric citrate allows the implementation of a broad range of doses.

Further, it is the intent of the invention to not be limited to capsules and tablets as oral formulations. It is known in the art that a wide variety of oral formulations may be adapted for use with the invention.

Illustrative Example of a Dosage Regimen

An non-limiting example of a dosing regimen is provided below. This is not meant to limit the invention as to how an effective amount of ferric citrate is selected, or the form in which it is provided or the frequency of administering the composition per day. The following merely illustrates how ferric citrate and placebo may be administered; e.g., as 500 mg capsules of identical appearance. All patients may receive (in a blinded fashion) 4 capsules with each of three meals, on a daily basis, for 28 days. Patients will be instructed to take the study medication within 10 minutes of finishing their meals (breakfast, lunch, and dinner).

The number of placebo, and active capsules to be taken at each meal, are as follows:

Placebo arm of the study
  4 placebo capsules, with breakfast
  4 placebo capsules, with lunch
  4 placebo capsules with dinner
Ferric citrate 2 g per day arm of the study
  1 ferric citrate capsule and 3 placebo capsules with breakfast
  1 ferric citrate capsule and 3 placebo capsules with lunch
  2 ferric citrate capsules and 2 placebo capsules with dinner
Ferric citrate 4 g per day arm
  2 ferric citrate capsules and 2 placebo capsules with breakfast 3 ferric citrate capsule and 1 placebo capsule with lunch
3 ferric citrate capsules and 1 placebo capsule with dinner
Ferric citrate 6 g per day arm
4 ferric citrate capsules with breakfast
4 ferric citrate capsules with lunch
4 ferric citrate capsules with dinner Clinical Schedule and Assessments Each patient's participation in the trial lasts for up to 8 weeks: the screening period (approximately 1-2 weeks), a 1-2 week washout, and 4 weeks of treatment with study medication.

Screening Visit 1 (Study Days −30 to −15)

The following procedures will be performed at the first screening visit:

1. Medical history, including concomitant medications.
2. Demographic data.
3. Physical examination, including height, weight, and vital signs.
4. Dietary interview, using 24 hour recall method, to assess dietary intake of calcium and phosphorous, three times during screening period, to include one dialysis day, one non-dialysis day, and one weekend day. Note: Dietary interview may be also performed, in part or in whole, during the washout period.
5. Laboratory assessment:
   a. Hematology: complete blood count (CBC) with differential, platelets.
   b. Chemistries: sodium, potassium, chloride, bicarbonate, blood urea nitrogen (BUN), creatinine, glucose (random), aspartate transaminase (AST), alanine transaminase (ALT), alkaline phosphatase (ALP), total bilirubin, total protein, albumin, serum calcium, serum phosphate, magnesium
   c. Total and LDL cholesterol levels
   d. Serum (3-HCG for women of childbearing potential
   e. Iron panel: serum iron, ferritin, transferrin saturation percentage, and total iron binding capacity.
6. 12-lead ECG.
7. Patients will be given instructions for the Washout Period (Study Days −14 to −1):
   a. All phosphate-binding agents will be discontinued at Day −14
   b. Any iron therapy (oral or intravenous) will be discontinued at Day −14
   c. Patients who have been receiving a stable dose of vitamin D or calcitriol for I month prior to enrollment will be instructed to maintain their current dose throughout the study
   d. Patients will be advised to avoid changes in diet, calcium or magnesium containing antacids (other medications).

Screening Visit 2 (Study Days −7+/−1 day)

Laboratory Assessment of serum $PO_4$. Patients with a Day −7 serum $PO_4$ 5.5 mg/dL and ≤10 mg/dL may be randomized before the 2-week washout is complete. The day of randomization will automatically become Day 0. Patients with a Day −7 phosphate level of 10 mg/dL will be removed from the study and instructed to resume their pre-study medications.

Study Day 0 (Randomization and Dosing)

1. Physical examination, including weight and vital signs.
2. Adverse event query.
3. Concomitant medication query.
4. Baseline Laboratory assessments:
   a. Serum PO4;
   b. Serum Ca;
   c. Iron panel: serum iron, ferritin, transferrin saturation percentage, and total iron binding capacity. The Baseline Laboratory Assessments may be done up to 3 days prior to Day 0.
5. Patients with a $PO_4$ level 0.5 mg/dL and ≤10 mg/dL will be randomized and a 15-day supply of study medication will be dispensed. Patients should be instructed to begin taking study medication within 10 minutes of completing their next meal on Day 0.

Study Day 14 (Midpoint Evaluation)

The following procedures will be performed at Study Day 14+/−1 day.

1. Physical examination including weight and vital signs.
2. Adverse event query.
3. Concomitant medication query.
4. Dispense an additional 15-day supply of study medication. All returned capsules should be counted and recorded in the Case Report Form.
5. Laboratory assessment:
   a. Hematology: CBC with differential, platelets.
   b. Chemistries: sodium, potassium, chloride, bicarbonate, BUN, creatinine, glucose (random), AST, ALT, ALP, total bilirubin, total protein, albumin, calcium, phosphate, magnesium.
   c. Iron panel: serum iron, ferritin, transferrin saturation percentage, and total iron binding capacity.
   d. Total and LDL cholesterol levels.

Note: Patients with a Day 14 phosphate level of >10 mg/dL will be removed from the study and instructed to resume their pre-study medications.

Study Day 28 (End of Study Evaluation)

The following procedures will be performed at Study Day 28+/−1 day or on the day of early termination.

1. Physical examination including weight and vital signs
2. Adverse event query.
3. Concomitant medication query.
4. Laboratory assessment:
   a. Hematology: CBC with differential, platelets
   b. Chemistries: sodium, potassium, chloride, bicarbonate, BUN, creatinine, glucose (random), AST, ALT, ALP, total bilirubin, total protein, albumin, calcium, phosphate, magnesium.
   c. Total and LDL cholesterol levels
   d. Iron panel: serum iron, ferritin, transferrin saturation percentage, and total iron binding capacity.
5. 12-lead ECG
6. Patients will be instructed to resume their pre-study medications after completing the study.

Data Management and Analysis

GloboMax will be the primary data management, monitoring, and coordinating center. Case report forms (CRF) will be provided for each subject. Subjects will not be identified by name or initials on CRFs. The CRF will be monitored at the clinical sites and collected by GloboMax's study monitor. Audited CRFs will be used to create electronic data files.

Three major categories of endpoints reflect biochemical and clinical issues being addressed at the outset. Additional clinical and biochemical issues are addressed as they arise. Therefore, the endpoints are not meant to limit the totality of relevant findings and measurements collected in these, or future studies.

Primary Endpoints

The change in serum $PO_4$ concentration at Days 14 and 28 from baseline.

Secondary Endpoints

The change in serum calcium concentration at Days 14 and 28 from baseline.

The change in iron, ferritin, transferrin saturation percentage, and total iron binding capacity at Days 14 and 28 from baseline.

The change in the Ca'PO$_4$ product at Days 14 and 28 from baseline.

Safety Endpoints

Safety will be monitored by recording adverse events and the results of physical examinations, vital signs and laboratory tests at each study visit.

Specific rules for withdrawal from the study, based on laboratory data, have also been set up to ensure patient safety.

A nonlimiting example of such criteria is illustrated by the following:

If a patient's serum phosphate level increases to ≥10 mg/dL at any time during the study period, the patient will be withdrawn from the study.

Example 4

Randomized, Double-Blind, Placebo-Controlled, Dose-Ranging Study of the Effects of Ferric Citrate on Serum Phosphate in Patients with End Stage Renal Disease (ESRD)

Objectives: (1) To determine the effect of ferric citrate at doses of 2, 4 and 6 g daily, administered TID (three times a day), for 28 days on serum phosphate (PO4) levels in patients with end stage renal disease (ESRD). (2) To evaluate the safety of ferric citrate at doses of 2, 4, 6 g daily, administered TID, for 28 days in patients with ESRD.

Study Drug: Ferric citrate disclosed in U.S. Ser. No. 11/206,981 and WO 2004/07444.

Study Design: Randomized, double-blind, placebo-controlled, dose-ranging study to assess the effect of ferric citrate on serum phosphate concentrations in patients with ESRD on hemodialysis. Patients are assessed at Study Days 14 and 28 for effectiveness as measured by serum phosphate concentrations. Patients who received one or more doses of study medication are also assessed for safety.

Study Duration: 8 weeks (including the screening period, 2 weeks washout, 4 weeks treatment)

Results show a decrease in serum PO4 and Ca*PO4 at 0, 2, and 6 gm/day (given as TID immediately after meals, i.e., within 10 minutes). Ferric citrate is administered orally, and is given equally three times a day.

The ability of ferric citrate to lower the serum phosphate levels in patients with ESRD was demonstrated. No significant change was observed in the serum calcium level during the 28 days for placebo, 2, 4, and 6 gm/day. However, the Ca*PO4 levels have decreased and were statistically significant for 6 gm/day dose at both 14 and 28 days. The results also indicate that calcification may be reversed or stabilized following treatment with ferric citrate. The Tables below summarize the data the study.

TABLE 3

Summary of Results

|  | Dose Response | Statistical Significant | Linear Regression |
|---|---|---|---|
| Serum PO4 (mg/dL) |  |  |  |
| Day 14 | No | No | P = 0.0523 |
| Day 28 | Yes | Yes (6 g/day) | P = 0.0073 |
| Serum Ca (mg/dL) |  |  |  |
| Day 14 | No | No | N.S. |
| Day 28 | No | No | N.S. |
| Ca × PO4 (mg/dL)$^2$ |  |  |  |
| Day 14 | Yes | No | P = 0.0401 |
| Day 28 | Yes | Yes (6 g/day) | P = 0.0158 |

*N.S.: Not Significant

TABLE 4

Summary of Serum [PO4] (mg/dL)

|  | Placebo (N = 16) | 2 g/day (N = 31) | 4 g/day (N = 32) | 6 g/day (N = 32) | Dose Response |
|---|---|---|---|---|---|
| Serum [PO4] (mg/dL) at Day 0 | 7.1 ± 1.43 | 7.1 ± 1.23 | 7.1 ± 1.27 | 7.3 ± 1.33 | N/A |
| Serum [PO4] (mg/dL) at Day 14 | 6.7 ± 1.22 | 6.7 ± 1.50 | 6.4 ± 1.56 | 6.3 ± 1.72 | No (P = 0.0523) |
| Serum [PO4] (mg/dL) at Day 28 | 7.2 ± 1.19 | 6.9 ± 2.22 | 6.0 ± 1.33 | 5.8 ± 1.76* | Yes |

*P < 0.05, Significant Difference Baseline Change as Compared to Placebo

TABLE 5

Summary of Serum [Ca] (mg/dL)

|  | Placebo (N = 16) | 2 g/day (N = 31) | 4 g/day (N = 32) | 6 g/day (N = 32) | Dose Response |
|---|---|---|---|---|---|
| Serum [Ca] (mg/dL) at Day 0 | 8.71 ± 0.779 | 8.78 ± 0.981 | 9.02 ± 0.913 | 8.99 ± 0.812 | No |
| Serum [Ca] (mg/dL) at Day 14 | 8.91 ± 0.782 | 9.01 ± 1.232 | 9.47 ± 0.990 | 9.13 ± 0.909 | No |
| Serum [Ca] (mg/dL) at Day 28 | 8.74 ± 0.830 | 9.00 ± 0.953 | 9.29 ± 0.960 | 9.26 ± 0.865 | No |

*P < 0.05, Significant Difference Baseline Change as Compared to Placebo

TABLE 6

Summary of Serum [Ca]* [PO4](mg/dL) 2

| | Placebo (N = 16) | 2 g/day (N = 31) | 4 g/day (N = 32) | 6 g/day (N = 32) | Dose Response |
|---|---|---|---|---|---|
| [Ca] * [PO4] (mg/dL)$^2$ at Day 0 | 62.8 ± 13.91 | 62.9 ± 13.25 | 63.5 ± 10.69 | 65.8 ± 12.19 | N/A |
| [Ca] * [PO4] (mg/dL)$^2$ at Day 14 | 59.9 ± 12.19 | 60.3 ± 16.50 | 59.9 ± 13.89 | 57.5 ± 16.27 | Yes |
| [Ca] * [PO4] (mg/dL)$^2$ at Day 28 | 63.2 ± 12.55 | 61.7 ± 21.25 | 55.4 ± 13.36 | 54.1 ± 17.68* | Yes |

*P < 0.05, Significant Difference Baseline Change as Compared to Placebo

TABLE 7

Treatment-Emergent Adverse Events

| | Placebo (N = 16) # Event (%) | 2 g/day (N = 33) # Event (%) | 4 g/day (N = 34) # Event (%) | 6 g/day (N = 33) # Event (%) |
|---|---|---|---|---|
| Total number of subjects with at least one adverse event (T#at1 AE) Sorted by Preferred Term (PT) | 7 (43.8) | 16 (48.5) | 12 (35.3) | 17 (51.5) |
| Abdominal Pain | 0 (0.0) | 0 (0.0) | 4 (11.8) | 2 (6.1) |
| Diarrhea | 2 (12.5) | 3 (9.1) | 1 (2.9) | 1 (3.0) |
| Sorted by System Organ Class/PT | | | | |
| GI Disorders (see above PT) | 4 (25.0) | 8 (24.2) | 10 (29.4) | 10 (30.3) |
| General Disorders | 2 (12.5) | 4 (12.1) | 2 (5.9) | 4 (12.1) |
| Infections and Infestations | 2 (12.5) | 0 (0.0) | 3 (8.8) | 1 (3.0) |
| Skin and SC Tissue Disorders | 0 (0.0) | 3 (9.1) | 0 (0.0) | 4 (12.1) |
| Sorted by SOC/PT/Severity | | | | |
| T#at1 AE, Mild | 7 (43.8) | 13 (39.4) | 9 (26.5) | 14 (42.4) |
| T#at1 AE, Moderate | 0 (0.0) | 6 (18.2) | 3 (8.8) | 2 (6.1) |
| T#at1 AE, Severe | 1 (6.3) | 0 (0.0) | 2 (5.9) | 1 (3.0) |
| GI Disorders, Mild | 4 (25.0) | 6 (18.2) | 8 (23.5) | 9 (27.3) |
| Sorted by SOC/PT/Relationship | | | | |
| T#at1 AE, Definitely | 0 (0.0) | 0 (0.0) | 0 (0.0) | 0 (0.0) |
| T#at1 AE, Probably | 1 (6.3) | 2 (6.1) | 2 (5.9) | 5 (15.2) |
| T#at1 AE, Possibly | 3 (18.8) | 5 (15.2) | 6 (17.6) | 2 (6.1) |
| GI Disorder, Definitely | 0 (0.0) | 0 (0.0) | 0 (0.0) | 0 (0.0) |
| GI Disorder, Probably | 1 (6.3) | 2 (6.1) | 2 (5.9) | 5 (15.2) |
| GI Disorder, Possibly | 3 (18.8) | 3 (9.1) | 6 (17.6) | 1 (3.0) |

As shown in FIGS. 2 and 3, treatments using pharmaceutical-grade ferric citrate provide several advantages over chemical grade ferric citrate. In general, while pharmaceutical-grade ferric citrate demonstrates an efficacy approximately equal to that of chemical grade ferric citrate, it achieves this result with less adverse side effects than chemical grade ferric citrate.

FIG. 2 also indicates that adverse side effects associated with administering pharmaceutical-grade ferric citrate were not statistically different from those associated with the placebo. An advantage of this safety profile is that an individual patient may have his dosing of pharmaceutical-grade ferric citrate titrated over a broad range of doses with less concern about side effect. In this way, a patient's individual treatment may be tailored to suit his specific needs and tolerances.

Decrease in Serum Creatinine Level

Glomerular filtration rate (GFR) level correlates with structural kidney damage and is used as a golden standard to measure kidney function. GFR can be estimated by the biomarkers serum creatinine. As renal function deteriorates, kidney lost its function to excrete creatinine effectively and lead to creatinine retention in the body. Therefore, increase of serum creatinine indicates lowering GFR and is an important sign of kidney deterioration.

In an open-label extension of a Phase II clinical study: "randomized, double-blind, placebo-controlled, dose-ranging study of the effects of ferric citrate on serum phosphate in patients with end stage renal disease (ESRD)", some of the patients were administered 2~6 g/day of ferric citrate and serum creatinine level was monitored to assess kidney function. Several patients who received 6 g/day of ferric citrate appear to have a trend of decreased serum creatinine level, which implies ferric citrate may modify, delay, and arrest or prevent the progression chronic kidney disease. Results from 2 patients are shown in FIGS. 5-6.

What is claimed is:

1. A method of treating chronic kidney disease, comprising administering a therapeutically effective amount of ferric citrate to a subject in need thereof.

2. The method of claim 1, wherein the ferric citrate has a BET active surface area selected from at least 16 m2/g and 16 m2/g to 20 m2/g.

3. The method of claim 1, wherein the ferric citrate has an intrinsic dissolution rate selected from at least 2 mg/cm2/min and 2 to 4 mg/cm2/min.

4. The method of claim 1, wherein the subject is a human.

5. The method of claim 1, wherein the clinical stage of chronic kidney disease is selected from stage 1, stage 2, stage 3, stage 4, and stage 5 (end stage renal disease).

6. The method of claim 1, wherein the subject is undergoing dialysis.

7. The method of claim 1, wherein the ferric citrate is administered at a dose of 2 g/day to 20 g/day.

8. The method of claim 1, wherein the ferric citrate is administered orally.

9. The method of claim 8, wherein the ferric citrate is formulated as a tablet, a powder, a capsule or a granule.

10. The method of claim 1, wherein the ferric citrate is administered at a dose of 1 g/day to 15 g/day.

11. The method of claim 1, wherein the ferric citrate is administered at a dose of 2 g/day, 4 g/day, 6 g/day, or 8 g/day.

12. The method of claim 1, wherein the ferric citrate is administered at a dose of 3 g/day.

13. The method of claim 1, wherein the ferric citrate is administered at a dose of 6 g/day.

14. The method of claim 8, wherein the ferric citrate is formulated as a tablet.

\* \* \* \* \*